(12) United States Patent
Seifalian

(10) Patent No.: US 8,858,631 B2
(45) Date of Patent: Oct. 14, 2014

(54) SYNTHETIC SCAFFOLDS AND ORGAN AND TISSUE TRANSPLANTATION

(75) Inventor: Alexander M. Seifalian, London (GB)

(73) Assignee: UCL Business PLC (GB)

( * ) Notice: Subject to any disclaimer, the term of this patent is extended or adjusted under 35 U.S.C. 154(b) by 30 days.

(21) Appl. No.: 13/542,202

(22) Filed: Jul. 5, 2012

(65) Prior Publication Data

US 2013/0066438 A1 Mar. 14, 2013

Related U.S. Application Data

(60) Provisional application No. 61/505,096, filed on Jul. 6, 2011.

(51) Int. Cl.
*A61F 2/20* (2006.01)
*A61F 2/04* (2013.01)
*A61L 27/18* (2006.01)
*A61L 27/38* (2006.01)
*A61F 2/02* (2006.01)
*A61L 27/54* (2006.01)
*A61L 27/36* (2006.01)

(52) U.S. Cl.
CPC ............ *A61F 2/04* (2013.01); *A61F 2230/006* (2013.01); *A61L 27/18* (2013.01); *A61L 27/3834* (2013.01); *A61L 2300/414* (2013.01); *A61F 2002/046* (2013.01); *A61F 2/02* (2013.01); *A61L 27/54* (2013.01); *A61L 27/3882* (2013.01); *A61L 2430/22* (2013.01); *A61L 27/3813* (2013.01); *A61L 2400/12* (2013.01); *A61L 27/3679* (2013.01)
USPC ............................................................ 623/9

(58) Field of Classification Search
USPC ............................................................ 623/9
See application file for complete search history.

(56) References Cited

U.S. PATENT DOCUMENTS

| 5,258,027 | A | 11/1993 | Berghaus |
| 7,820,769 | B2 | 10/2010 | Seifalian et al. |
| 8,158,728 | B2 * | 4/2012 | Desimone et al. ............ 525/403 |
| 8,303,656 | B2 * | 11/2012 | Shadduck .................... 623/6.13 |
| 8,435,283 | B2 * | 5/2013 | Jordan et al. ................. 623/1.18 |
| 8,506,648 | B2 * | 8/2013 | Loomas et al. ............ 623/23.65 |
| 2006/0069425 | A1 * | 3/2006 | Hillis et al. .................. 623/1.16 |
| 2006/0074382 | A1 * | 4/2006 | Gonzalez et al. .......... 604/93.01 |
| 2009/0138077 | A1 * | 5/2009 | Weber et al. ................. 623/1.46 |
| 2010/0076555 | A1 * | 3/2010 | Marten et al. ..................... 623/9 |
| 2010/0331954 | A1 * | 12/2010 | Sahatjian et al. ............ 623/1.11 |
| 2011/0054591 | A1 * | 3/2011 | Sahatjian et al. ............ 623/1.15 |

FOREIGN PATENT DOCUMENTS

WO WO 2008/157362 12/2008

OTHER PUBLICATIONS

P. Jungebluth, et al, Tracheobronchial Transplantation With a Stem-Cell-Seeded Bioartificial Nanocomposite: A Proof-Of-Concept Study, Lancet (2011) vol. 378, p. 1997-2004.
M. Kalathur, et al., Translating Tissue-Engineered Tracheal Replacement From Bench to Bedside, Cellular and Molecular Life Sciences (2010) vol. 67, p. 4185-4196.

(Continued)

*Primary Examiner* — Suzette J Gherbi
(74) *Attorney, Agent, or Firm* — Vedder Price, P.C.; Thomas J. Kowalski; Deborah L. Lu

(57) ABSTRACT

Articles, compositions, and methods for growing tissues and organs using bioreactors, including rotating bioreactors, are provided. Synthetic scaffolds for growing artificial tissue and organ transplants are also provided.

18 Claims, 6 Drawing Sheets

(56) References Cited

OTHER PUBLICATIONS

R. Kannan, et al., Silsesquioxane Nanocomposites as Tissue Implants, Plastic and Reconstructive Surgery (2007) vol. 119, No. 6, p. 1653-1662.

A. Kidane, et al., A Novel Nanocomposite Polymer for Development of Synthetic Heart Valve Leaflets, Acta Biomaterialia (2009) vol. 5, p. 2409-2417.

S. Sarkar, et al., Manufacture of Small Calibre Quadruple Lamina Vascular Bypass Grafts Using a Novel Automated Extrusion-Phase-Inversion Method and Nanocomposite Polymer, Journal of Biomechanics (2009) vol. 42, p. 722-730.

T. Sato, et al., Biodegradable Polymer Coating Promotes the Epithelization of Tissue-Engineered Airway Prostheses, Journal of Thoracic and Cardiovascular Surgery (2010) vol. 139, No. 1, p. 26-31.

A. Seifalian, Editorial: Manufacturing Living Organs Using Tissue Engineering Strategy, Biotechnology and Applied Biochemistry (2011) vol. 58, No. 5, p. 285-287.

* cited by examiner

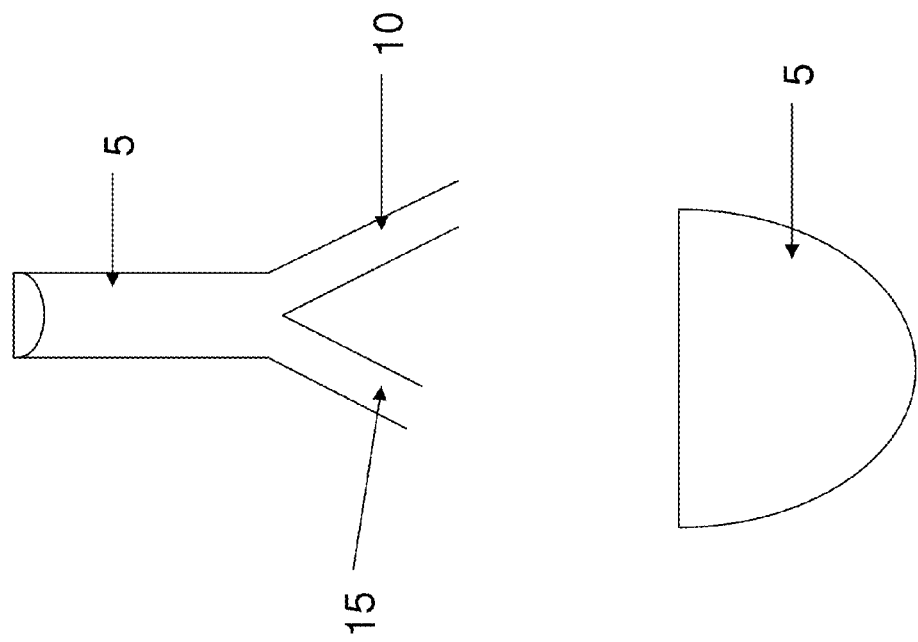

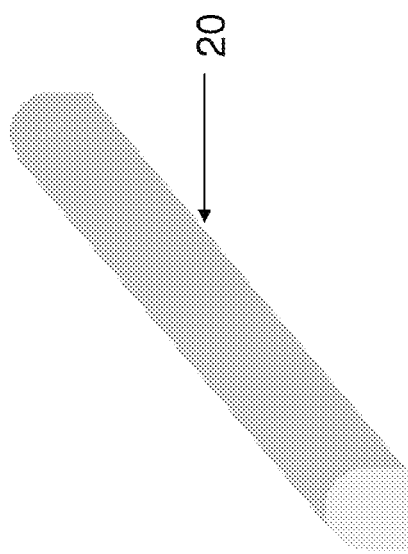
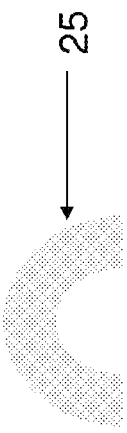
FIG 3A
FIG 3B

US 8,858,631 B2

SYNTHETIC SCAFFOLDS AND ORGAN AND TISSUE TRANSPLANTATION

RELATED APPLICATIONS AND INCORPORATION BY REFERENCE

This application claims priority to U.S. provisional patent Ser. No. 61/505,096 filed Jul. 6, 2011.

The foregoing applications, and all documents cited therein or during their prosecution ("appln cited documents") and all documents cited or referenced in the appln cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention. More specifically, all referenced documents are incorporated by reference to the same extent as if each individual document was specifically and individually indicated to be incorporated by reference.

FIELD OF INVENTION

The present invention relates generally to techniques for growing and transplanting tissues and organs, and, more specifically, to growing and transplanting artificial airways.

BACKGROUND

Patients suffering from localized airway tissue damage often can be treated surgically to remove the damaged (e.g., diseased) tissue. For example, a cancerous lesion in tracheal or bronchial tissue is typically removed via surgical resection. However, in some instances the extent of tissue damage is too large for surgical resection to be possible. For example, endoscopic and radiological evaluation of a patient's trachea may show that the length of residual healthy airway would be too small after removal of the diseased tissue. Also, the location of disease pathology may make it difficult or impossible to remove diseased tissue and effectively resect the remaining healthy tissue. For example, it can be difficult to restore appropriate branch geometry after removal of diseased tissue that includes all or part of the tracheal/bronchial branch.

If effective surgical resection is not feasible, a tissue transplant may be used to replace the excised tissue. For example, tracheal tissue transplants have been performed using natural tracheal tissue from a donor, or using synthetic tracheal tissue grown on a natural tissue scaffold.

However, compatible donor tissue often is not available, and unpredictable risks of disease and rejection are associated with the use of donor tissue. Also, depending on the patient's health status, there may not be sufficient time to prepare an implant grown on a natural scaffold. Furthermore, it can be difficult to grow large or complex regions of synthetic tissue using a natural scaffold.

Citation or identification of any document in this application is not an admission that such document is available as prior art to the present invention.

SUMMARY OF THE INVENTION

In some embodiments, aspects of the invention provide methods, devices, and compositions for preparing artificial airway tissues for transplantation into a patient in order to replace diseased or damaged tissue that has been surgically removed.

A schematic overview of a non-limiting procedure for generating and replacing airway tissue using synthetic biocompatible molds is provided in FIG. 1.

Initially, a subject may be evaluated using one or more imaging techniques to identify the location and extent of damaged tissue that needs to be removed. Prior to surgery, a biocompatible mold may be produced to conform to the size and shape of the tissue being removed. The mold may be tailor-made based on the size and shape of the patient's anatomy of the specific tissue. Alternatively, an available mold of a compatible size and geometry may be used. Once the mold is selected, it may be seeded on both its external and luminal surfaces with compatible cells that retain at least some ability to differentiate. In some embodiments, the cells may be autologous cells (e.g., mononuclear cells) that may be isolated from the patient (e.g., from the patient bone marrow) or a compatible donor. The seeding process may take place in a bioreactor (e.g., a rotating bioreactor) for a few days prior to surgery. Just prior to surgery, additional cells may be added to the luminal surface of a synthetic tissue. In some embodiments, these cells may be epithelial cells, which may be isolated from the patient's airway if the tissue is an airway tissue. Just prior to surgery, one or more growth factors may be added to the synthetic tissue. The synthetic tissue may then be transplanted into the patient to replace the damaged tissue that is removed. The patient is monitored post-surgery for signs of rejection or of a poorly functional airway transplant.

It should be appreciated that not all of these procedures may not be required for every transplant surgery. Any one or more of these procedures may be useful alone or in combination to assist in the preparation and/or transplantation of a synthetic organ or tissue. Accordingly, in some embodiments, aspects of the invention relate to producing a synthetic scaffold suitable for replacing an airway or portion thereof (e.g., a trachea or portion thereof, a bronchus or portion thereof, or a combination thereof). In some embodiments, aspects of the invention relate to seeding synthetic airway scaffolds with appropriate cells for implantation into a subject. In some embodiments, aspects of the invention relate to preparing a synthetic airway for surgical implantation, including providing growth factors for promoting appropriate cell or tissue differentiation.

In general, a scaffold for an airway implant can be a conduit shaped to represent the region of the airway that is being replaced. In some embodiments, the conduit is cylindrical. However, in some embodiments, the conduit can be formed to have the natural shape of an airway region. For example, in cross-section the conduit may have a D shape, as illustrated in FIG. 2B, with a convex anterior (e.g., U-shaped) and a relatively straight posterior. The length of the scaffold can be designed to match (or be slightly longer than) the length of the airway region being replaced. In some embodiments, a scaffold can be modeled on that of the patient that is to receive the implant. Accordingly, the dimensions and shape of the scaffold can be designed to match those of the airway region being replaced. It should be appreciated that depending on the region that is being replaced, the overall shape of the scaffold may be a straight conduit, a Y-shaped bifurcated conduit, or an L-shaped conduit.

In an advantageous embodiment, the tissue is an airway tissue, advantageously a trachea, a bronchus and/or any segment of an airway tissue. In this embodiment, the synthetic scaffold may be suitable for replacing an airway or a portion thereof (e.g., a trachea or portion thereof, a bronchus or portion thereof, or a combination thereof).

In some embodiments, kits containing one or more components described herein may be provided.

In some embodiments, aspects of the invention relate to methods of producing a synthetic scaffold for replacing a tissue or portion thereof, the methods which may comprise placing one or more structural ribs on an airway mold, wherein each structural rib comprises a first material, coating the airway mold and structural ribs with a second material, and solidifying the second material to form a conduit that comprises the structural ribs. The tissue may be an airway tissue.

In some embodiments, the first material may be a set POSS-PCU nanocomposite material. In some embodiments, the second material may be a POSS-PCU fluid and the solidifying may comprise coagulating the POSS-PCU fluid. In some embodiments, the airway mold may comprise a convex anterior and a straight posterior. In some embodiments, each structural rib may be U-shaped. In some embodiments, the airway mold may be a glass, stainless steel, or PTFE mold. In some embodiments, each structural rib may be about 0.5 cm thick. In some embodiments, the structural ribs may be separated by about 0.5 cms along the length of the airway mold. In some embodiments, the airway mold may be a tracheal mold having a diameter of approximately 2-3 cm. In some embodiments, each structural rib may have an internal width of about 2-3 cm. In some embodiments, the airway mold may be a bronchial mold having a diameter of approximately 1-1.5 cm. In some embodiments, each structural rib may have an internal width of about 1-1.5 cm.

In some advantageous embodiments, the airway mold may be branched and may include one tracheal segment and two bronchial segments. In some embodiments, the airway mold may include a detachable bronchial segment.

In some embodiments, the conduit may be porous. In some embodiments, the second material may be a POSS-PCU polymer fluid that may comprise salt crystals, and wherein the POSS-PCU polymer may be coagulated in an aqueous solution, and wherein the salt crystals may be dissolved after coagulation to form pores. In some embodiments, the average pore diameter may be about 20-100 microns. In some embodiments, the average pore diameter may be about 40 microns. In some embodiments, the salt may be sodium bicarbonate.

In some embodiments, aspects of the invention relate to methods of seeding a synthetic airway scaffold, the methods may comprise incubating a synthetic airway scaffold in a rotating bioreactor in the presence of a cellular solution.

In some embodiments, the synthetic airway scaffold may be produced according to any one of methods described herein. In some embodiments, the cells may be mesenchymal cells. In some embodiments, the cells may be obtained from human bone marrow.

In some embodiments, the incubating may last for 1-3 days. In some embodiments, the incubating may last for 2 days. In some embodiments, the incubating may be at a temperature of between about 25 C and 37 C. In some embodiments, the temperature may be about 30 C. In some embodiments, the temperature may be about 35 C. In some embodiments, the methods may further comprise adding epithelial cells.

In some embodiments, aspects of the invention relate to methods of preparing a seeded synthetic scaffold for transplantation, the method which may comprise adding one or more growth factors to the seeded scaffold.

In some embodiments, the synthetic scaffold may be produced according to any one of the methods described herein. In some embodiments, the scaffold may be seeded according to any one of the methods described herein. In some embodiments, a first growth factor may be added to a structural rib of the synthetic scaffold. In some embodiments, the first growth factor may promote cartilage formation. In some embodiments, the first growth factor may be TGF-β. In some embodiments, the first growth factor may be injected into the structural rib. In some embodiments, a second growth factor may be added to the wall of the synthetic scaffold. In some embodiments, the second growth factor may promote cell mobilization and proliferation. In some embodiments, the second growth factor may be GCSF. In some embodiments, the methods may further comprise adding EPO to the seeded synthetic scaffold, wherein EPO may be added in an amount sufficient to prevent apoptosis.

Accordingly, it is an object of the invention to not encompass within the invention any previously known product, process of making the product, or method of using the product such that Applicants reserve the right and hereby disclose a disclaimer of any previously known product, process, or method. It is further noted that the invention does not intend to encompass within the scope of the invention any product, process, or making of the product or method of using the product, which does not meet the written description and enablement requirements of the USPTO (35 U.S.C. §112, first paragraph) or the EPO (Article 83 of the EPC), such that Applicants reserve the right and hereby disclose a disclaimer of any previously described product, process of making the product, or method of using the product.

It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

These and other embodiments are disclosed or are obvious from and encompassed by, the following Detailed Description.

BRIEF DESCRIPTION OF THE DRAWINGS

The following detailed description, given by way of example, but not intended to limit the invention solely to the specific embodiments described, may best be understood in conjunction with the accompanying drawings.

FIG. 2A is schematic diagram showing the trachea and bronchi portions of a patient's airway;

FIG. 2B is a schematic diagram showing a cross-sectional view of a trachea;

FIG. 3A is a schematic diagram showing a tracheal mold;

FIG. 3B is a schematic diagram showing a synthetic rib;

DETAILED DESCRIPTION

Figure 1:
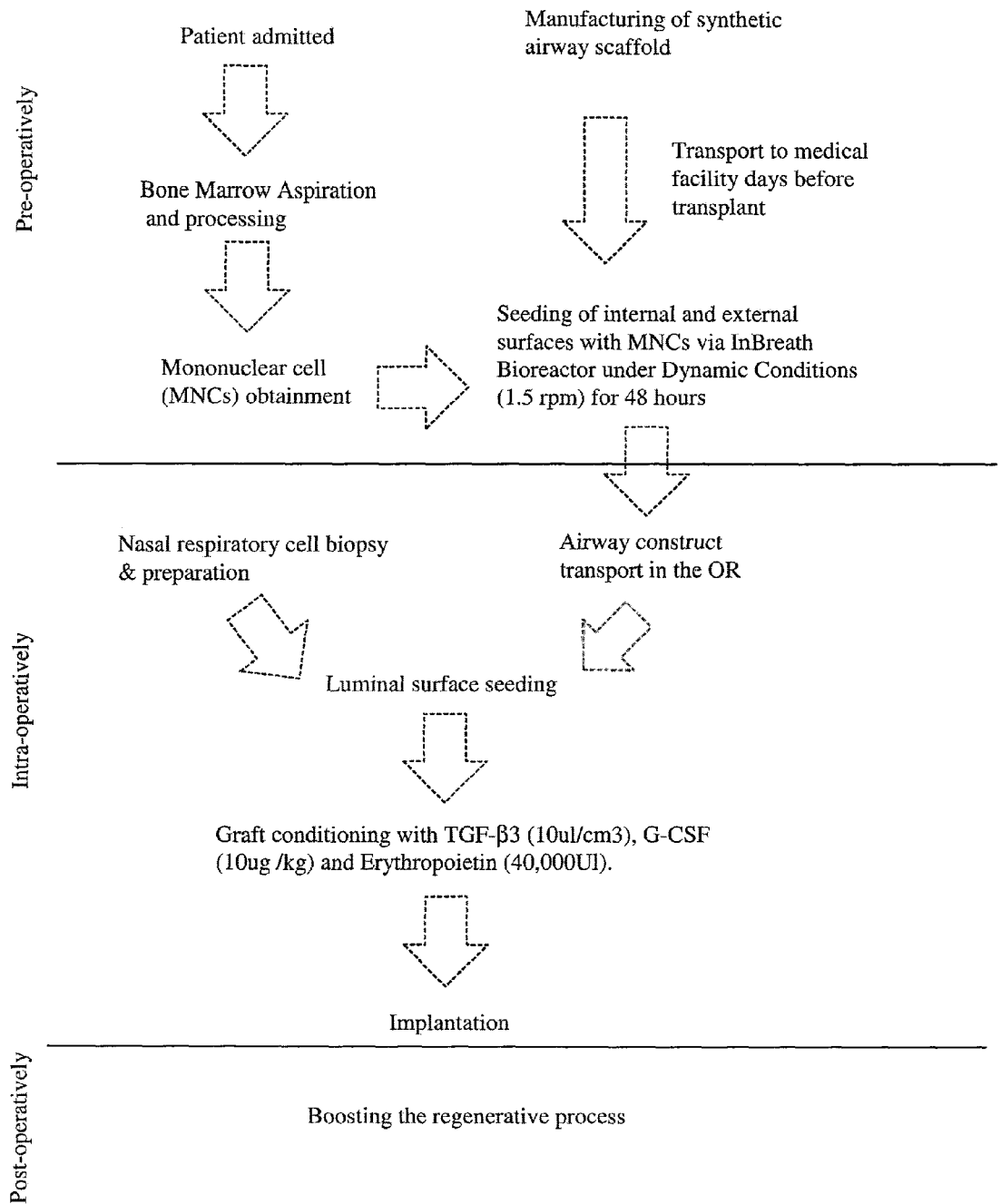
FIG. 1 is a flow-chart that outlines a non-limiting embodiment of a surgical procedure for replacing a portion of an airway using an artificial scaffold.

The present invention relates generally to articles, compositions, and methods for growing and implanting tissues and organs, and, more specifically, to using bioreactors for growing tissues for implantation into a subject. In some embodiments, aspects of the invention relate to producing a synthetic scaffold suitable for replacing a tissue or portion thereof. In some embodiments, aspects of the invention relate to seeding synthetic scaffolds with appropriate cells for implantation into a subject. In some embodiments, aspects of the invention relate to preparing a synthetic tissue for surgical implantation, including providing growth factors for promoting appropriate cell or tissue differentiation.

In an advantageous embodiment, the tissue may be an airway tissue (e.g., a trachea or portion thereof, a bronchus or portion thereof, or a combination thereof) and the synthetic scaffolds may be synthetic airway scaffolds. It should be appreciated that aspects described herein in the context of synthetic airway tissue also may be applied to other synthetic tissues and organs.

In an advantageous embodiment, aspects of the invention relate to methods, compositions, and articles for preparing and transplanting synthetic scaffold-based implants that are sufficient to support effective airway function in a patient after removal of a portion of the patient's airway.

In some embodiments, the articles, compositions, and methods may be used to form biocompatible structures for tissue engineering and organ replacement, advantageously for airway replacement. The subject matter of the present invention involves, in some cases, interrelated products, alternative solutions to a particular problem, and/or a plurality of different uses of one or more systems and/or articles. Aspects of the invention may also relate to transplanting cells, tissues, organ-like structures, and/or complete organs into a recipient patient (e.g., a human patient).

The present invention relates to tissue replacement, advantageously connective tissue replacement. The present invention also relates to organ replacement. In particular, the invention is particularly suitable for tissue and/or organ replacement in which the tissue and/or organ comprises a matrix, advantageously an extracellular matrix.

In an advantageous embodiment, a synthetic scaffold is designed and produced to replace a portion of a trachea and/or a bronchus in a patient. A synthetic scaffold can have the same shape as a natural airway (e.g., trachea, bronchus, or combination thereof), and can be manufactured to have substantially similar physical properties (e.g., elasticity, tensile strength, etc.).

The natural trachea is a cartilaginous and membranous tube that extends from the lower part of the larynx (at the level of the sixth cervical vertebra) to the upper border of the fifth thoracic vertebra, where it branches to form the two bronchi. The trachea has the shape of a cylinder that is flattened at the back (posterior). The front (anterior) is convex. A typical adult human trachea is just over 10 cm long, and about 2-2.5 cm wide. However, it is generally larger in males and smaller in females.

The right bronchus is about 2.5 cm long, and the first branch from the bronchus to the upper lobe of the right lung is about 2 cm away from the trachea. The left bronchus is narrower but at about 5 cm long, it is longer than the right bronchus.

FIG. 2A shows a front view of a trachea (5), the branch region (6), and left and right bronchi (10 and 15 respectively).

The trachea and extrapulmonary bronchi contain a series of imperfect horizontal rings of cartilage that support fibrous and muscular tissue, and mucous membrane, that together form the tracheal or bronchial tube. There are approximately 16-20 cartilaginous rings in a trachea. Each is typically about 4 mm deep, 1 mm thick, and is located in approximately the anterior two thirds of the circumference of a trachea. The overall configuration of the cartilaginous support rings in the bronchi is similar. The rings are slightly smaller than those in the trachea, and there are about 6-8 in the right bronchus, and about 9-12 in the left bronchus.

Synthetic scaffolds can be produced to have the same overall dimension, shape, and configuration, of natural trachea and bronchi (including the branch region). In some embodiments, one or more structural features (e.g., features that mimic natural structural features) can be included in a synthetic scaffold. For example, one or more structural rings (e.g., imperfect rings) can be included to support the walls of a synthetic tracheal and/or bronchial scaffold. However, it should be appreciated that the precise size and/or shape of the rings does not need to be identical to those of natural rings, provided they provide similar structural support properties.

In some embodiments, a synthetic scaffold is produced to replace a portion of an airway (e.g., a portion of a trachea and/or a bronchus) in a subject. The synthetic scaffold can be designed to be patient-specific by using structural information about the airway region that is being replaced in the patient. Structural information can be obtained from any suitable imaging technique, including, but not limited to, imaging scans and/or bronchoscopy analyses of the patient's airway, including the diseased region. However, it should be appreciated that generic scaffolds also may be produced and used for patients. For example, an appropriate scaffold for a patient may be selected from alternative generic scaffolds of different sizes and shapes.

In some embodiments, a synthetic scaffold may be based on polymeric material that is formed on a mold. The mold may be shaped and/or sized to be patient-specific. Alternatively, the mold may be of a predetermined generic shape and/or size as discussed above and elsewhere herein.

In some embodiments, the polymeric material is based on polyhedral oligomeric silsesquioxane (POSS) covalently bonded to poly(carbonate-urea)urethane (PCU) to form a nanocomposite that is fully haemo- and biocompatible. The polymer is referred to herein as a POSS-PCU polymer. A liquid preparation of POSS-PCU polymer can be solidified using different techniques resulting in nanocomposites having different structural properties. In some embodiments, a POSS-PCU polymer can be cast in a mold using heat treatment to form a cast nanocomposite. In some embodiments, a POSS-PCU polymer can be coagulated upon exposure to an aqueous solution (e.g., deionized water) to form a coagulated nanocomposite. POSS-PCU polymers are useful, because they are biocompatible, non-toxic, and non-immunogenic. They also support cell growth effectively. Details of POSS-PCU polymers are known in the art, including, for example in U.S. Pat. No. 7,820,769, issued Oct. 26, 2010, the contents of which are incorporated herein by reference.

However, it should be appreciated that other polymers can be used as aspects of the invention are not limited to particular polymers. In some embodiments, a suitable polymer may be any biocompatible, non-toxic, and/or non-immunogenic polymer that can be produced to have appropriate physical properties (e.g., appropriate elasticity, flexibility, tensile strength, etc.) or any combination thereof. It should be appreciated that a wide range of mechanical properties can be acceptable. In some embodiments, polymers that have properties that are similar to those of human trachea and/or bronchi are used.

Materials which may be utilized for the polymers of the present invention include, but are not limited to, polylactic acid (PLA), polyglycolic acid (PGA), polycaprolactone (PCL), proteic materials such as collagen or fibrin, polysaccharidic materials such as chitosan or glycosaminoglycans (GAGs) including hyaluronic acid possibly in combination with cross linking agents such as glutaraldehyde or carbodiimide or tissue extracts lacking cells.

In some embodiments, a biodegradable polymer can be used in addition to, or instead of, a non-degradable polymer. In certain embodiments, for example for pediatric applications, a biodegradable polymer is used to replace one or more portions of a child's trachea and/or bronchus.

In some embodiments, an example of a biodegradable polymer that can be used is POSSPCL ((POSS modified Poly(caprolactone/carbonate) urethane/urea)). POSS-PCL polymers are known in the art. See, for example, Raghunath J, Georgiou G, Armitage D, Nazhat S N, Sales K M, Butler P E, Seifalian A M, *Degradation studies on biodegradable nanocomposite based on polycaprolactone/polycarbonate (80:20%) polyhedral oligomeric silsesquioxane*, J. Biomed Mater Res A. 2009 December; 91(3):834-44. PubMed PMID: 19051308; Raghunath J, Zhang H. Edirisinghe M J, Darbyshire A, Butler P E, Seifalian A M, *A new biodegradable nanocomposite based on polyhedral oligomeric silsesquioxane nanocages: cytocompatibility and investigation into electrohydrodynamic jet fabrication techniques for tissue-engineered scaffolds*, Biotechnol Appl Biochem. 2009 January; 52(Pt 1):1-8. PubMed PMID: 18402554; and Gupta A, Vara D S, Punshon G, Sales K M, Winslet M C, Seifalian A M, *In vitro small intestinal epithelial cell growth on a nanocomposite polycaprolactone scaffold*, Biotechnol Appl Biochem. 2009 Dec. 4; 54(4):221-9. PubMed PMID: 19860739; PubMed Central PMCID: PMC2825731, the disclosures of each of which are incorporated herein by reference.

In some embodiments, a mold has a generally cylindrical shape. However, a mold may have the shape of a trachea that is flattened posteriorly. Accordingly, the cross-sectional shape of the mold may be approximated to a D, with the flattened portion representing the posterior of the trachea and the front of the curved portion representing the anterior of the trachea (see FIG. 3A). Similar structural considerations may be used for molds used to generate one or more bronchial regions. In some embodiments, the mold may be slightly tapered to represent the progressive narrowing of the trachea or bronchus along its proximal-distal length. However, in some embodiments, the diameter of the mold may be uniform along the length of the tracheal or bronchial region that is being replaced. Nonetheless, the diameter of a mold for a trachea is typically wider than the diameter of a mold for a bronchus (at least within the same patient). In some embodiments, a mold represents a linear portion of an airway, a branched (e.g., Y-shaped) portion of an airway, a curved or bent (e.g., L-shaped) portion of an airway, or a combination thereof, depending on the location and extent of airway tissue that is being removed.

In some embodiments, a mold may be solid or hollow, or contain a combination of solid and hollow portions, provided that the outer region of the mold provides a surface having an appropriate shape and size for forming a synthetic scaffold.

In some embodiments, a synthetic scaffold is designed to include one or more structural features (e.g., ribs, ridges, rings, or any other structural reinforcements) to prevent the scaffold from collapsing. The supporting structures may be synthetic imperfect rings (e.g., C or U shaped structures or other rib-like structures) that will support the connective walls of the synthetic scaffold. A non-limiting example of a structural rib is illustrated in FIG. 3B. In some embodiments, synthetic supports may be designed to mimic the cartilage ribs of a natural airway.

Figure 3C:
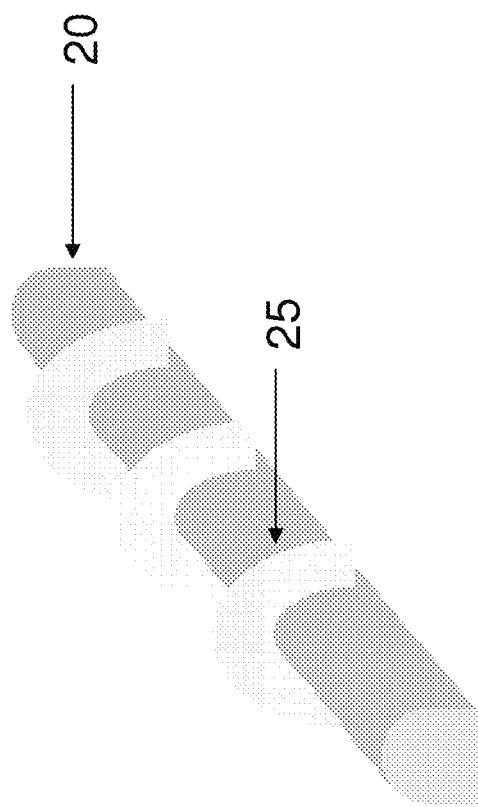
FIG. 3C is a schematic diagram showing a series of synthetic ribs placed on a tracheal mold.
Figure 3D:
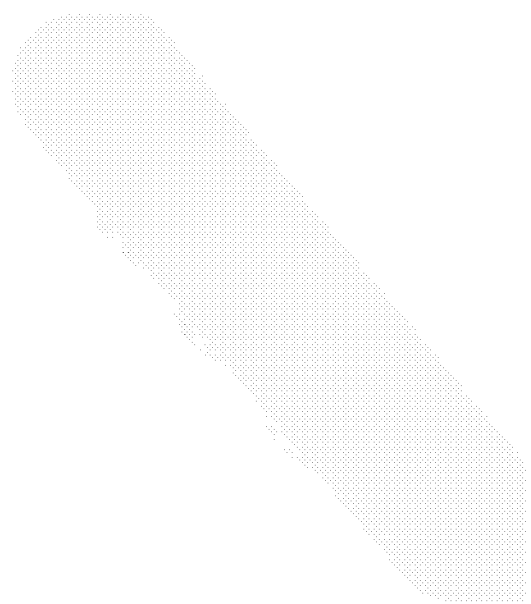
FIG. 3D is a schematic diagram showing a tracheal mold with several structural ribs and an overlay of synthetic material that will form the connective walls.

In some embodiments, a method of generating a synthetic scaffold that includes structural rings (e.g., incomplete rings) can involve a multi-step synthesis process. Initially, one or more structural supports (e.g., ribs or rings) are prepared from a first material (e.g., a set polymer). The structural supports then may be placed on the outside of an airway mold (e.g., a cylindrical or approximately cylindrical mold having the shape of a trachea). For example, a series of C or U-shaped supports may be placed in parallel along the mold (as illustrated in FIG. 3C). Subsequently, a layer of a second material (e.g., a polymer fluid) is applied to the surface of the mold and attached to the structural support (as illustrated in FIG. 3D). In some embodiments, the second material is a polymer fluid (e.g., a POSS-PCU fluid). The polymer fluid can be applied using any suitable technique. The fluid is then solidified using any appropriate technique (e.g., coagulated, set, or polymerized, etc.) to form a thin layer of synthetic material that incorporates the structural ribs. The resulting synthetic scaffold can be removed from the mold and includes a conduit formed by an outer wall that incorporates a plurality of structural support elements.

It should be appreciated that the first material (the material of the structural supports) and the second material (the material of the wall membrane) can be the same or different.

In some embodiments, the first material is a set POSS-PCU nanocomposite. This polymer may be set using any suitable method (for example, heating using conditions known in the art). In some embodiments, the structural supports are prepared using a mold for the C or U rings.

In some embodiments, the second material is a coagulated POSS-PCU nanocomposite. This polymer may be coagulated by contact with an aqueous solution, for example, deionized water. In some embodiments, a mold along with one or more structural rings is dipped into a POSS-PCU polymer fluid. This coats the mold and the structural rings. The coated mold is then dipped into an aqueous solution (e.g., deionized water) under conditions to promote coagulation, resulting in a tubular polymeric structure that incorporates the structural rings (see FIG. 3C).

As a result the different types of polymer material have different structural properties, the cast material is more rigid and has a higher tensile strength. In contrast, the connective wall may have a spongier physical property that is more suited for the flexibility required of the connective material.

In some embodiments, the connective material is prepared in such a way that it is porous. For example, the polymer material may be mixed with a salt prior to coagulation. After coagulation, the salt crystals are dissolved (e.g., in the aqueous solution used to coagulate the polymer) resulting in open pores. It should be appreciated that any suitable salt may be used.

The salt may be a sodium salt, a lithium salt or a potassium salt. The salt may be a carbonate or bicarbonate salt, such as but not limited to, calcium carbonate, cobalt(II) carbonate, copper(II) carbonate, lanthanum carbonate, lead carbonate, lithium carbonate, magnesium carbonate, manganese(II) carbonate, nickel(II) carbonate, potassium carbonate or sodium carbonate.

In an advantageous embodiment, Na bicarbonate salts are used. It also should be appreciated that the size of the salt crystals that are used determines the size of the resulting pores. Salt crystals can be sized using any suitable technique and salt crystals of predetermined average dimension may be selected. The size of the selected pore may be based in part on the cell type that is to be added to the material. In some embodiments, an average pore size of about 40 microns is used. However, pore sizes ranging from about 1 nm to about 500 microns may be used (e.g., pores having an average diameter of about 10 nm to about 1 micron, about 1 to about 10 microns, about 10 to about 100 microns, about 10 to about 50 microns, about 50 to about 100 microns, about 100 to about 200 microns, about 200 to about 500 microns, or other suitable size). Different cell types grow more effectively in the presence of different pore sizes. For example, chondrocytes grow well in the context of about 50-100 micron pores.

In some embodiments, the amount of salt used can be adjusted in order to adjust the pore frequency (as opposed to the average pore size). In some embodiments, the polymer fluid contains 50% sodium bicarbonate having an average crystal size of about 40 microns.

It should be appreciated that the spacing of the support rings along the length of an artificial airway region can be any spacing that is sufficient to provide structural support. For example, ribs of about 0.5 cm thick may be spaced about 0.5 cm apart along the length of the artificial airway.

In some embodiments, the size of the graft may be longer than the size of the diseased tissue in order to provide a surgeon with additional tissue that can be useful for suturing and/or tailoring the size to the amount of tissue that is removed during surgery. However, the diameter of the graft should be about the diameter of the patient tissue. In some embodiments, a diameter of approximately 30 mm (e.g., 29, 30, or 31 mm) is used for a tracheal segment. In some embodiments, a diameter of approximately 15 mm (e.g., 14, 15, or 16 mm) is used for a bronchial segment.

Figure 4:
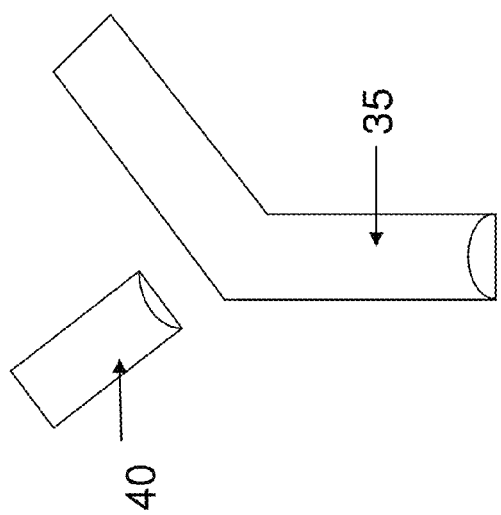
FIG. 4 is a schematic diagram showing a mold that can be used to form a Y-shaped scaffold.

In some embodiments, a mold may be a relatively straight mold for a tracheal or bronchial airway segment. However, in some embodiments, a mold may be a bifurcated mold (e.g., Y-shaped mold) that is used to prepare tissue for the transplant that covers the tracheal to bronchial branching region. In some embodiments, it may be challenging to remove a Y-shaped mold without damaging the scaffold, regardless of its elasticity. Accordingly, a Y-shaped mold may be formed using two relatively straight sections that can be reversibly attached at an angle (see FIG. 4). The two straight regions then may be separated after polymer formation and independently removed without damaging the scaffold. For example, the first branch may be removed followed by the second one. The first and second straight sections may be attached using any appropriate technique (e.g., using a screw, a peg, or any other type of reversible attachment).

In some embodiments, a mold for the rings or for the wall may be made of any suitable material or combination of materials (glass, stainless steel, PTFE, aluminum, other alloy or any other suitable material, or any combination thereof).

In some embodiments, a mold may be sterilized using any suitable technique, for example irradiation, heating, chemical sterilization, or any combination thereof.

It should be appreciated that other techniques may be used to deposit the polymer on the surface of the mold. Non-limiting examples include electro spinning and atomization. For example, ultrasound atomization may be used to produce a spray that can be deposited on the mold. Once deposited, the polymer may then be coagulated using any appropriate technique such as dipping in an aqueous solution.

In some embodiments, the wall thickness of the scaffold can be controlled by using different concentrations of polymer. A higher concentration of polymer results in a thicker wall.

In some embodiments, the polymeric scaffold may be sterilized prior to use. Any suitable sterilization technique may be used, for example irradiation, heating, chemical sterilization, or a combination thereof.

It should be appreciated that other techniques may be used to generate structural regions in a synthetic scaffold. In some embodiments, an outer surface of a mold may include one or more depressions, indents, ridges, channels and/or other structural features that can be used to form a scaffold having regions of different thicknesses. Regions of greater thickness may be used to provide structural support for the scaffold.

Alternative systems and techniques for fabricating scaffolds include, but are not limited to, molding, three-dimensional printing (e.g., three-dimensional layering), multi-photon lithography, stereo lithography (SLA), selective laser sintering (SLS) or laser ablation, ballistic particle manufacturing (BPM), and fusion deposition modeling (FDM). Other fabrication techniques are also possible.

In some embodiments, molecular modeling may be used to design a scaffold. Prototype scaffolds may be tested to determine their structural properties and their resilience. For example, one or more stretching, squashing, and/or bending tests may be performed. In some embodiments, many cycles of stretching, squashing, bending, or other physical tests may be performed and the physical properties of the scaffold may be evaluated over time (e.g., after thousands to millions of cycles) to determine when the physical structure of the scaffold deteriorates. In some embodiments, a scaffold can withstand several million cycles (e.g., several hundred million cycles).

In some embodiments, desired physical parameters (e.g., flexibility, tensile strength, etc.) may be used to determine appropriate thicknesses to use for different regions of the scaffold.

Examples of scaffolds are illustrated herein in the context of scaffolds for human airways. However, it should be appreciated that similar techniques and materials may be used for airway scaffolds for non-human animal or mammal species. The dimensions may be different due to the different sizes and anatomies of different animals.

Accordingly, scaffolds may be porous or substantially non-porous. In some instances, the wall of a scaffold includes pores having a cross-sectional dimension of less than or equal to 1 mm, less than or equal to about 100 microns, less than or equal to 50 about microns, less than or equal to about 40 microns, less than or equal to about 30 microns, less than or equal to about 10 microns, less than or equal to about 5 microns, less than or equal to about 1 micron, or less than or equal to about 100 nm. A variety of techniques can be used for introducing porosity into a scaffold. For instance, porosity can be induced by methods such as solution casting, emulsion casting, polymer blending, and phase transition induced porosity.

The tracheal systems may be advantageously manufactured with a porosity of about 40 μm to enhance the regeneration of trachea with the attachment and proliferation of autologous undifferentiated stem and respiratory cells. This polymer has been shown to support the attachment and proliferation of many different cell types including human mesenchymal stem cells and epithelial cells specific for the trachea.

Scaffolds can have various dimensions which may depend on the particular use of the scaffold. A scaffold may have an average thickness of, for example, between about 1 micron and about 1 mm, between about 10 microns and about 0.5 mm, between about 1 mm and about 5 cm, between about 1 mm and about 1 cm, between about 1 cm and about 10 cm, or between about 1 cm and about 5 cm. Other thicknesses are also possible. The largest cross-sectional dimension of the scaffold can also vary from, for example, between about 1 micron and about 1 mm, between about 10 microns and about 0.5 mm, between about 1 mm and about 5 cm, between about 1 mm and about 1 cm, between about 1 cm and about 10 cm, between about 1 cm and about 5 cm, between about 1 cm and about 20 cm, or between about 10 cm and about 20 cm. A length of the scaffold can also vary from, for example, between about 1 mm and about 5 cm, between about 1 cm and about 10 cm, between about 1 cm and about 5 cm, between about 1 cm and about 20 cm, or between about 10 cm and about 20 cm. Other lengths are also possible. A scaffold may also have an aspect ratio (length to average cross sectional dimension) of at least about 2:1, about 3:1, about 5:1, or about 10:1 or more. It also should be appreciated that the size and thickness of a scaffold may vary along its length. In some embodiments, a scaffold may include a series of zones of different thicknesses (e.g., forming a series of rings that alternate between two different thicknesses).

Optionally, surface properties of a scaffold can be modified by various techniques. For example, in some cases, surfaces of a scaffold can be modified by coating and/or printing an additive proximate the structure. Surfaces may be modified with additives such as proteins and/or other suitable surface-modifying substances. For example, collagen, fibronectin, an RGD peptide, and/or other extracellular matrix (ECM) proteins or growth factors can be coated onto the scaffold, e.g., to elicit an appropriate biological response from cells, including cell attachment, migration, proliferation, differentiation, and gene expression. Cells can then be seeded onto surfaces of the scaffold. In one embodiment, cell adhesion proteins can be incorporated into certain portions of a scaffold to facilitate ingrowth of blood vessels. In another embodiment, growth factors can be incorporated into the scaffold to induce optimal cell growth conditions that trigger healthy tissue formation within certain regions of the scaffold. In other cases, additives can be incorporated into the material used to form the scaffold (e.g., embedded in the scaffold during fabrication).

In some cases, it may be desirable to modify all or portions of a scaffold with a material that inhibits cell adhesion, such as a surfactant (e.g., polyethylene glycol and polypropylene oxide-polyethylene oxide block copolymers). For instance, areas of a scaffold where it is not desirable for cellular growth can be coated with such materials, i.e., to prevent excessive soft connective tissue ingrowth into the structure from the surrounding tissue. In some cases, modification of surface properties of the scaffold can be used to position cells at specific sites on or within the scaffold. In some embodiments, a combination of cell-adhering and cell-inhibiting substances can be incorporated into various portions of a scaffold to simultaneously facilitate and inhibit cell growth, respectively.

In some embodiments, a scaffold can be coated with a porous material (e.g., a polymer such as a gel), e.g., prior to or during the seeding of cells. A porous polymer coating a scaffold can be used for a variety of purposes. For example, a porous polymer may be used to form pores on a scaffold that is otherwise non-porous. The porous polymer may allow, for example, sustained release of an active agent from the scaffold, e.g., to facilitate cell growth and/or cell adhesion as a function of time.

As described herein, cells may be seeded on various portions of a scaffold either before or after the scaffold is positioned in a bioreactor. In certain embodiments, cells may be seeded on at least one surface of a scaffold.

Scaffolds may be sterilized using any appropriate technique, including heat treatment, irradiation, chemical treatment, or other sterilization technique. However, it should be appreciated that the choice of sterilization technique may impact the physical properties of a scaffold material. For example, a POSS-PCU based scaffold appears to be less flexible after sterilization for 20 minutes at 134 C, relative to sterilization for 20 minutes at 121 C. These different properties may affect how to attach the scaffold to a bioreactor or which sutures to use for surgery, for example.

Methods described herein may further comprise using a rotating bioreactor to seed a plurality of cells by rotating the scaffold in a liquid containing the plurality of cells.

In certain embodiments, a rotating bioreactor comprises a vessel or chamber within which the scaffold may be removably positioned, and wherein the scaffold can be configured to rotate about a central longitudinal axis. A bioreactor may include a vessel that is removably positioned within the bioreactor. The bioreactor may include a support for mounting the scaffold and a motor for rotating the support. In some embodiments, a bioreactor may also include a temperature control system for monitoring and/or controlling a temperature of a fluid inside a vessel. The bioreactor may further include a thermocouple and/or a resistance temperature detector for sensing a temperature of the contents inside the vessel. The thermocouple may be operatively connected to the temperature controller to control temperature of the contents in the vessel.

The bioreactors described above and herein may include a vessel that is removably positioned within the bioreactor. In such and other embodiments, the vessel can be removed from the housing and transported while being maintained in a sterile environment. In yet other embodiments, an entire bioreactor system is portable and can be transported during or after a desired process.

In certain embodiments, a motor and/or temperature control system operatively associated with a bioreactor described herein is portable along with the bioreactor itself, and optionally along with any pumps, connectors, and/or sources of fluids. The control system may include, for example, all or many of the necessary controls and functions required to perform a fluidic manipulation (e.g., temperature control, mixing, and performing reactions) in the bioreactor. The control system may be manipulated remotely in some embodiments. Advantageously, such and other portable control systems can be programmed with set instructions, and, if desired, transported (optionally with the bioreactor) and hooked up to the bioreactor, ready to perform a process by an end user. In some embodiments, the bioreactor and any associated systems may be placed on a wheeled support for easy transport (e.g., from a GMP facility to a surgical facility). In some embodiments, a power supply also may be included so that the rotation and/or temperature control of the bioreactor can be controlled during transport (e.g., between different facilities within a hospital).

In some embodiments, a vessel includes a cover that is removably positioned on top of remaining portions of the vessel. The cover may enclose the vessel so as to provide a sterile environment within the vessel. The cover may simply sit on top of the walls of the vessel, similar to how a cover of a petri dish sits on top of the petri dish, or the cover may be attached to the vessel by intervening components such as hinges, seals, locks, magnets, and the like.

In some embodiments, a bioreactor vessel can be sealed to maintain sterility and/or prevent fluid from spilling during transport. For example, a bioreactor may incorporate one or more structural features (e.g., clips, flanges, seals, etc.) that allow the cover to be sealed to the body of the vessel or chamber during transport.

A scaffold may be attached to the rotating support of the bioreactor using any suitable method. In some embodiments, the open ends of the trachea and/or bronchi are placed over circular (or substantially circular, e.g., having the cross-sectional shape of a trachea) support discs at either end of the rotating support structure. In some embodiments, the open ends may be sutured or otherwise attached to the discs. However, this is not necessary if there is sufficient friction between the edges of the discs and the inner surface of the scaffold walls at one or both ends. In some embodiments, the rotating support structure may include one or more longitudinal support rods that can support the scaffold along its length.

In some embodiments, prior to transplanting the scaffold into a patient, the scaffold is seeded with one or more different cell types. The cells can be derived from the patient. In some embodiments, cell samples that contain stem cells or other cell types capable of growth and/or differentiation may be used to seed the scaffold. For example, autologous stem cells may be derived from the patient bone marrow. In some embodiments, cell samples that contain epithelial cells may be used to seed the scaffold. For example, autologous epithelial cells may be derived from the patient's airway passages (e.g., nasal passages). However, it should be appreciated that any suitable cell types (for example autologous cells or immunocompatible cells) may be used to seed the scaffold.

Seeding may be performed under conditions of fluid flow over the scaffold surface. For example, seeding may be performed in a rotating bioreactor. The rotation of the scaffold through a cellular solution promotes efficient cell seeding. In certain bioreactors, both the outer and luminal surfaces of the scaffold are exposed to the cellular solution and both are seeded. Typically, a volume of seeding solution is used such that it only partially fills the bioreactor chamber (e.g., about 40% to about 60% full). As a result, the artificial scaffold is partially submerged and partially exposed at any given time. However, rotation of the scaffold through the liquid ensures that the entire inner and outer surfaces of the scaffold are exposed to cells in the seeding solution. Rotation may be performed at any suitable speed (e.g., about 1-5 rotations per minute, or other suitable speed). During seeding, the bioreactor is kept sterile and a suitable temperature is maintained to promote cell seeding and growth.

After a seeding/growth period, the seeded scaffold is transplanted into a patient. This process may involve transferring the scaffold from a growth center to an operating room. In some embodiments, the bioreactor chamber may be transferred under sterile conditions. However, in some embodiments, an entire bioreactor system may be transferred, including the chamber and associated devices for maintaining temperature and rotation, as described above. In some embodiments, the entire system is provided on a mobile support (e.g., an apparatus with wheels) that can readily be moved from one part of a hospital to another. In some embodiments, the device is designed to maintain sterility and avoid spills during the transfer. Accordingly, liquid containers (e.g., the growth chamber, any liquid reservoirs, and any connecting or sampling chambers) may be provided with a sealable opening (e.g., a sealable lid) that can be sealed prior to transfer to the operating room.

It should be appreciated that the extent of time used for seeding and/or growth in a bioreactor may depend on the viability of the cells, the number of cells required, the health of the patient, and other practical considerations. In some embodiments, a seeding period of about 2 days (e.g., around 48 hours) is sufficient to provide sufficient cell seeding for effective transplantation. This is shorter than previously tested. However, it has been found that this short period of time provides sufficient seeding for the artificial airway to be transplanted into the patient. However, other seeding times may be used as aspects of the invention are not limited in this respect.

Prior to surgery, an artificial tissue and/or organ may be further prepared by "boosting" it with appropriate agents (e.g., growth factors) to promote cell proliferation, cell differentiation, and/or to prevent cell death (e.g., via apoptosis). In some embodiments, the growth factors or other agents may be applied to the surface of all or part of the scaffold. In some embodiments, one or more growth factors or other agents may be applied locally (e.g., on or in the structural ribs) to promote local cellular differentiation (e.g., cartilage formation). In some embodiments, the growth factors or other agents may be injected into the scaffold material (e.g., into one or more structural rings or ribs). Accordingly, one or more agents may be suffused into a scaffold prior to surgery (e.g., prior to seeding, and/or after seeding, but before transplantation).

In some embodiments, GCSF or a recombinant form thereof is applied over the entire surface of the scaffold to promote cell growth and progenitor cell mobilization after surgery. GCSF may be applied using any suitable technique, for example using a syringe to deliver a GCSF solution. However, other techniques (for example using a brush, a sponge, or other applicator) may be used. In some embodiments, TGF-$\beta$ or a recombinant form thereof is applied to the structural rings to promote cartilage formation by mesenchymal cells attached to the structural rings. In some embodiments, a solution containing the growth factor is injected into the rings. However, other delivery techniques may be used. In some embodiments, EPO or a recombinant form thereof is used to prevent apoptosis (relatively high levels of EPO have been shown to prevent apoptosis as opposed to promoting red blood cell formation). In some embodiments, EPO is applied (e.g., injected) near the anastomosis.

It should be appreciated that one or more of these proteins may be used to boost natural scaffold (e.g., decellularized scaffolds). It also should be appreciated that one or more other agents (e.g., growth factors or other agents) may be applied to a portion or all of a scaffold depending on the purpose of the application and the functional properties of the agent being applied. Any of the agents described herein can be added to a scaffold or portion thereof using any suitable technique, including soaking, spraying, infusing, or coating.

In some embodiments, a scaffold is pretreated with one or more agents before cell seeding so that the agents do not need to be added at the time of surgery. Alternatively or in addition, one or more agents can be added after seeding (e.g., after removal from a rotating bioreactor) but before surgical transplantation.

In some embodiments, a scaffold or a portion thereof may be designed to incorporate one or more structural features that allow for efficient delivery and/or gradual release of the growth factor or other agent (regardless of whether the agent is added before or after seeding). For example, the structural ribs may contain a hollow portion, channel, depression or other volume into which an agent can be deposited. Accordingly, in some embodiments, a scaffold can include one or more zones that can act as depots or reservoirs for specific agents. These zones can be hollow zones, zones of higher porosity, or zones that have been surface-modified to be compatible with the agent(s) of interest. In some embodiments, instead of, or in addition to modifying the scaffold to include depot or reservoir zones, an external depot or reservoir containing the agent(s) of interest (for example, in the form of a gel, matrix, sac, or any combination thereof) can be placed on the surface of the scaffold (e.g., at one or more locations, or substantially covering the entire scaffold or portions thereof). In some embodiments, the agent(s) are contained within a slow or delayed release medium (e.g., mixed with a slow or delayed release matrix, or the depot or reservoir zones are bounded by walls that slowly release the agents) or that are biodegradable and do not release the agent(s) for a predetermined time. By controlling (e.g., delaying) the release of the agent(s), the cells can be seeded substantially in the absence of additional agents, and subsequently exposed to one or more agents (e.g., growth and/or differentiation factors) after sufficient time (e.g., 1, 2, 3, 4, 5 or more days) for the cells to seed and start proliferating. However, it should be appreciated that delayed release of agents is not always required. In some embodiments, it may be helpful to release certain agents (e.g., certain growth factors or antibiotics) throughout the initial seeding and growth phases.

In some embodiments, a scaffold contains one or more structural features that are particularly useful for adding agent(s). For example, a scaffold (or a portion thereof) may include channels that can be filled with solution containing agent(s) of interest. In some embodiments, the channels are surface channels. In some embodiments, a scaffold region (e.g., a structural ring) may include an internal hollow chamber or channel (e.g., running most or all of the internal length of the structural ring) that can be filled with an agent solution prior to surgery. In some embodiments, the channels (whether at the surface or internal) are in fluid connection with a loading zone that is structurally adapted to receive the delivery end of a loading device (e.g., the tip of a needle or other device that is used to deliver the agent solution).

Also, one or more structural features of a delivery device may be provided to assist in the delivery of an agent. For example, a syringe with a short needle may be used. In some embodiments, the length of the needle should be shorter than the thickness of the material into which the agent is being delivered. This avoids the complication of the needle penetrating through to the other side of the scaffold. In some embodiments, a needle or other delivery device may include an adjustable register to limit the depth to which the needle can penetrate.

In some embodiments, one or more agents are administered systemically to a patient prior to surgery. For example a growth factor (e.g., GCSF or a recombinant form thereof) may be administered to a patient prior to surgery (e.g., 1 day prior to surgery) to increase progenitor cell mobilization. However, other growth factors or other agents also may be administered prior to surgery to prepare the patient for the transplantation.

During surgery, the seeded scaffold is removed from the support structure of the bioreactor. In some embodiments, the scaffold is longer than the airway segment being removed (for example, it may contain an additional length of tissue at one or both ends). This allows a surgeon to cut the scaffold down to an appropriate size in situ, and also provides a sufficient length of synthetic material to effectively suture the scaffold to the remaining healthy tissue in the patient.

In some embodiments, the texture and physical properties of the scaffold may require that specific types of sutures be used. In some embodiments, a relatively wide and/or elastic suture is used to prevent or reduce damage to the scaffold material. Examples of suitable sutures include, but are not limited to, Vicryl 2-0 sutures.

In some embodiments, one or more agents are administered systemically to a patient after surgery. For example a growth factor (e.g., GCSF or a recombinant form thereof) may be administered to a patient after surgery (e.g., for several weeks after surgery, for example, for about 1, 2, 3, 4, or more weeks after surgery) to increase progenitor cell mobilization. However, other growth factors or other agents also may be administered prior to surgery to prepare the patient for the transplantation.

A patient also is monitored after surgery for signs of rejection, signs of cardiovascular distress, signs of respiratory distress, and/or for other physiological functions.

It should be appreciated that components of the molds and bioreactors described herein may be manufactured using metal, glass, rubber, plastic, composite, other natural or synthetic material, or any combination thereof. Where polymeric materials are used, such materials can be selected or formulated to have suitable physical/mechanical characteristics, for example, by tailoring the amounts of components of polymer blends, adjusting the degree of cross-linking (if any), etc. For instance, those of ordinary skill in the art can choose suitable polymers based on factors such as the polymer's compatibility with certain processing techniques, compatibility with any materials contained in the container (e.g., cells, nutrients, gases, etc.), compatibility with any treatments or pre-treatments (e.g., sterilization, autoclave), flexibility, puncture strength, tensile strength, liquid and gas permeabilities, and opacity.

In some embodiments, a portion of a bioreactor chamber, for example, the lid or cover, may be transparent to visible light to allow viewing and/or monitoring of contents inside the vessel during seeding.

Bioreactors, molds, or components thereof may be sterilized using any suitable technique prior to use.

In general, as used herein, a component of an inventive system that is "operatively associated with" or "operatively connected to" one or more other components indicates that such components are directly connected to each other, in direct physical contact with each other without being connected or attached to each other, or are not directly connected to each other or in contact with each other, but are mechanically, electrically (including via electromagnetic signals transmitted through space), or fluidically interconnected so as to cause or enable the components so associated to perform their intended functionality.

Although the present invention and its advantages have been described in detail, it should be understood that various changes, substitutions and alterations can be made herein without departing from the spirit and scope of the invention as defined in the appended claims.

The present invention will be further illustrated in the following Examples which are given for illustration purposes only and are not intended to limit the invention in any way.

EXAMPLES

Example 1

Production and Transplantation of a Biosynthetic-Scaffold-Based Tracheal/Bronchial Transplant FIG. 1 outlines a general surgical procedure using a biosynthetic scaffold to replace a portion of an airway. In this example, a transplantation of the trachea using a synthetic bioengineered scaffold reseeded with autologous undifferentiated stem and respiratory cells was used as an intraoperative solution for a 36 year old male with a primary malignant tumor of the trachea (mucoepidermoid). The patient had been maximally treated with radiation therapy (70 Gy).

Based on actual CT scans and bronchoscopy, the tumor involved the last 4 cm of the trachea along with the bifurcation (right main bronchus>than the left). This scenario represented a contraindication to any surgical reconstruction using standard techniques.

A synthetic bioengineered matrix, reseeded with autologous undifferentiated stem and (nasal) respiratory cells, of appropriate size and morphology, was prepared for transplantation. The transplant procedure allowed the airway tumor to be completely removed while preserving the right lung and safely reconstructing the airway and giving the patient a chance for cure and a normal quality of life.

Endoscopic and radiological evaluation of the patient trachea showed that the length of residual healthy airways and the localization and extension of the pathology made it impossible to perform a surgical resection of the pathological segment with a termino-terminal anastomosis (about 6 cm or 50% of airway length).

Pre-Operative Investigations:

Following tracheal evaluations, the patient was admitted to the hospital 3 to 4 days prior to transplantation. Clinical evaluations were performed prior to surgery, including: Computerized Tomography of the neck and chest as well as three-dimensional reconstruction of the airways; rigid bronchoscopy; evaluation of cardio-respiratory functions; blood count including blood coagulation factors and evaluation of the blood coagulation system; evaluation of liver and kidney functions; further diagnostic investigations and oncological-type staging if necessary, including biopsy of bone marrow to rule out micrometastatic disease; immunogenic evaluation by peripheral blood sample to determine HLA phenotype and serologic and genomic systems types; and evaluation of the basal level of the patient's haematopoietic stem cells. A sample of about 30 ml of peripheral blood is taken on admittance in order to evaluate the basal level of haematopoietic stem cells and a fraction of this sample will be frozen for further evaluation. Evaluation of the basic peripheral blood level of endogenous erythropoietin also was performed.

On the day before the transplant, the patient was started on a "boosting" therapy to mobilize cells by means of systemic injections of analogous recombinants of Granulocyte Colony-Stimulating Factor (Filgrastim, 10 µg/kg up to a maximum of 30 million U.I.) and Erythropoietin (Epoetina alpha or beta, up to a maximum of 40,000 U.I.) [9-11].

Bone Marrow Removal Procedure and Manipulation:

Two days before the transplant, bone marrow is harvested by means of bilateral multiple aspiration from the iliac crest for a total amount of 300 ml. This procedure is performed under spinal anesthesia and lasts about 60 minutes. The explanted material is gathered in a 600 ml transfer bag containing ACD in ratio 1:8. Mononuclear cells are obtained by separation on a Ficoll density gradient at a density of 1.077 g/ml. After separation, the cells are washed three times with a physiological solution (5% human albumin added) in order to eliminate residual Ficoll and to leave the cells in a solution that only contains components approved for clinical use. The whole procedure is carried out in a semiclosed system on a Cobe2991 (Caridian BCT). The final product, re-suspended with medium (medium+autologous serum 5% +antibiotics 1%) in a volume of 200 mL, is placed in a 600 ml transfer bag and taken to a GMP facility. A 5 ml volume is removed from the bag before clinical use to test for sterility and biological type. The material is tested for the following:

number of mononuclear cells (MNCs) (minimum amount $2\times10^6$ cells/mL);

cellular vitality by means of cytofluorometric analysis (7-AAD) (range 94-98%);

evaluation of mesenchymal progenitors CFU-F; and evaluation of haematopoietic progenitors CD34+.

A total of $15\times10^6$ cells is subdivided in three cryo-vials and frozen according to standard procedure in DMSO for subsequent analysis.

The same procedure also is performed on the day of the transplant but this time only 100 ml of bone marrow is collected and the end product is re-suspended to a volume of 50 ml.

Removal of Epithelial Respiratory Cells, Biopsy and Manipulation:

Respiratory cell biopsies are taken the day of the transplant, intraoperatively from the nasal fossa via a mucosectomy-biopsy (about 2 $cm^3$). An immediate frozen section is performed to rule out micrometastatic disease. The rest of the biopsied mucosa is kept in saline until implantation. Once the results of the frozen section are available, then the biopsied mucosa is fragmented and reseeded in the luminal surface of the tracheal construct. The purpose of this procedure is to boost re-epithelialization of the bioengineered graft.

Synthetic Scaffold:

A tailor-made synthetic bioengineered trachea was designed based on information from Computed Tomographic (CT) Scans and endoscopies. POSS-PCU polymers were developed to have mechanical and structural properties that simulate those of natural airways. The fabrication and composition of the polymer were designed to provide mechanical properties that avoid luminal collapse. In addition, polymers were developed to support the attachment and proliferation of tracheal specific cell types using appropriate pore sizes and polymer fabrication methods.

Modeling techniques were used to design a construct that will function as close as possible to the native trachea. The mechanical properties of POSS-PCU for casted materials include a maximum force of 65 MPa and an elongation at break of 920%. Coagulated POSS-PCU materials have a maximum force of 1.5 MPa and an elongation at break of 410%. It should be appreciated that the structural and mechanical properties of casted and coagulated POSS-PCU polymers can be fine-tuned to provide properties that are comparable to the natural airway scaffold of the trachea.

Artificial tracheal cartilage rings are prepared with mechanical properties similar to those of native trachea to provide mechanical strength and withstand collapsing of the trachea. These artificial rings are sandwiched in between coagulated POSS-PCU. The tracheal cartilage rings are placed at regular intervals on the mold in the exact shape of the patient's trachea, and then the coagulated POSS-PCU material is used to cover the rings on the inside and outside respectively. The tracheal systems are manufactured with a porosity of about 40 µm to enhance the regeneration of trachea with the attachment and proliferation of autologous undifferentiated stem and respiratory cells. This polymer has been shown to support the attachment and proliferation of many different cell types including human mesenchymal stem cells and epithelial cells specific for the trachea.

InBreath Bioreactor:

The work in the current protocol involves a bioreactor design previously utilized in a successful first-in-man implantation of a tissue-engineered large airway replacement. The device, commercialized under the name, InBreath 3D Organ Bioreactor, is designed for placement within a tissue culture incubator and consists of a modular polysulphone organ chamber, a motor unit, and a remote controller. The chamber is easily detachable from the motor unit and its polysulphone construction permits sterilization in standard laboratory autoclaves. The motor unit provides consistent rotation to the tissue holder within the chamber, ensuring controlled application of hydrodynamic shear forces to the developing tracheal construct. A fully enclosed motor housing protects the brushless DC motor from the corrosive moisture within the incubator. The remote control unit is placed outside the incubator providing a means to adjust rotational speed without disturbing the incubator environment.

In the previous work, a decellularized natural tracheal scaffold was used in combination with the Bioreactor. This scaffold was seeded on the intraluminal side with host epithelial cells and externally with chondrocytes differentiated from host bone marrow stem cells. The seeded construct was allowed to incubate in the bioreactor for several days prior to removal for implantation. In contrast, in the current protocol the synthetic scaffold is tailor-made to match the patient's anatomy using a synthetic material (POSS-PCU). As in the previous protocol, both internal and external surfaces of the scaffold are seeded within the bioreactor. However, in this case, autologous undifferentiated stem cells are used on both surfaces. Incubation time is reduced to 48 hours, and dynamic forces will be applied by rotating at 1.5 rpm. This incubation takes place during the 48 hours preceding the transplant procedure.

Airway Transplant:

Having performed the resection of the airway's damaged segment, the airway construct is seeded intraoperatively with the respiratory cell biopsies on the internal surface. The graft is then injected (conditioned) with growth factors including TGF-B3 (10 µl/cm$^2$) [13, 14], G-CSF (10 µg/kg), and Erythropoietin (40,000 UI) (to stimulate the mobilization of the peripheral haematopoietic cells) [9-11].

The implant is anastomosed proximally and distally so as to reconstruct the airway after removal of the defective tissue. The implant then is covered and wrapped by an omentum major flap (adipose vascularized tissue detached from the large bend of the stomach, harvested on the right or left gastroepiploic artery and then carried over to the mediastinum trans-diaphragmatically or sub-sternally) to guarantee long-term protection of the graft and of the anastomosis and to promote indirect neo-vascularisation of the graft.

Post-Operative Treatment:

To boost the regenerative process, the patient is treated pharmacologically during the post-operative period with systemic injections of a) analogous recombinants of GCSF (Filgrastin, 10 µg/kg up to a maximum of 30 million U.I.), and b) analogous synthetics of erythropoietin (epoetina alpha or beta up to a maximum of 40,000 U.I.).

Both factors are administered in suitable concentrations to stimulate the mobilization/recruitment of haematopoietic cells, in (regenerative) doses not associated with any side-effects [9-11, 15]. Every second day the plasma Erythropoietin level and the blood count (including the white blood cell formula) are monitored. Levels above 50-60,000 white blood cells are considered toxic and will result in a reduction/suspension of the therapy. Treatment is carried out every other day for 2 weeks following the transplant.

Patient Follow-Up:

The patient follow-up includes the following evaluations: endoscopic evaluation (flexible and/or rigid bronchoscopy) of the transplanted airway every day for the first week and every other day for the second week, after which once a month for the first six months, and every 6 months thereafter for the first 5 years; evaluation of the blood count with white blood cell formula every second day for the first two weeks; evaluation of the haemopoietic stem cells; every second day blood samples will be taken (5 ml) to evaluate the trend of haemopoietic stem cells present at the peripheral blood level; immunogenic evaluation (after 3, 7 and 30 days from the transplant, a blood sample will be taken to make a study of the histocompatibility by evaluating the antibodies); the immunogenic follow-up also will be carried out after 3, 6 and 12 months from the transplant; computerized tomography of the neck and chest with a three-dimensional reconstruction of the transplanted airway will be done at month 1, month 3 and month 6 of the follow-up, and every 6 months thereafter for the first 5 years; and oncological follow-up will be life-long, and includes the standard evaluations [16].

Example 2

Nanocomposite Bioengineered Airway Scaffold Material

The airway scaffold was designed using a synthetic material based on polyhedral oligomeric silsesquioxane (POSS) covalently bonded to poly(carbonate-urea)urethane (PCU) to form a nanocomposite that is fully haemo- and biocompatible.

The nano-topography surface of POSS-PCU nanocomposite polymers with elevated POSS nanocages and non-elevated PCU segments have been shown to promote cell proliferation. Extensive in vitro and in vivo validation studies on POSS-PCU have demonstrated that this nanocomposite polymer is non-toxic and biocompatible.

The POSS-PCU nanocomposite polymer has been extensively tested for its cytocompatibility, proving its ability to support the attachment and proliferation of numerous cell types including: chondrocytes, epithelial cells, mesenchymal stem cell, endothelial progenitor cells, and schwann cells.

The following experiments provide results for key cell types of a natural windpipe.

Chondrocytes:

Sheep derived nasal chondrocytes were seeded on a POSS nanocomposite, and their metabolic activity was measured at various time points using an Alamar Blue assay. The increase shows that the cells have attached and are proliferating. Tissue culture plastic was used as a control. Scanning electron microscopy image analysis was performed to confirm that the cells attached to the polymer. DAPI staining (DAPI stains the cell's nucleus) also was used to show that the cells grew on the nanocomposite.

Epithelial Cells:

Rat derived intestinal epithelial cells were seeded onto a POSS nanocomposite. The cells were cultured for 21 days, and the metabolic activity was measured at various time points. This shows that the cells attached and were viable and proliferated on the polymer. Also, SEM imaging of the in-growth of the cells into the polymer showed that the epithelial cell layer was seen to encroach into the pore from the surface, suggesting the in-growth of cells into the POSS-PCL polymer.

Human Bone Marrow-Derived Mesenchymal Stem Cells (hBM-MSCs):

hBM-MSCs were seeded on a POSS nanocomposite, and their metabolic activity was measured at various time points using an Alamar Blue assay. The increase shows that the cells have attached and are proliferating. Tissue culture plastic was used as a control. Also, scanning electron microscopy imaging confirmed that the cells had attached to the polymer.

Human Endothelial Progenitor Cells (hEPCs):

hEPCs were seeded onto a POSS nanocomposite. The cells were cultured for 35 days, measuring the metabolic activity at various time points. This shows that the cells have attached and stay viable for a minimum of 35 days. SEM imaging of the in-growth of the cells into the polymer also was performed.

REFERENCES

[1] Macchiarini P, Jungebluth P, Go T, et al. Clinical transplantation of a tissue-engineered airway. Lancet 2008; 372, 2023-2030.
[2] Kannan R Y, Salacinski H J, Sales K M, Butler P E, Seifalian A M. The endothelialization of polyhedral oligomeric silsesquioxane nanocomposites: an in vitro study. Cell Biochem Biophys 2006; 45:129-136
[3] Kannan R Y, Salacinski H J, De G J, et al. The antithrombogenic potential of a polyhedral oligomeric silsesquioxane (POSS) nanocomposite. Biomacromolecules 2006; 7:215-223
[4] Kannan R Y, Salacinski H J, Ghanavi J E, et al. Silsesquioxane nanocomposites as tissue implants. Plast Reconstr Surg 2007; 119:1653-1662
[5] Rashid S T, Fuller B, Hamilton G, Seifalian A M. Tissue engineering of a hybrid bypass graft for coronary and lower limb bypass surgery. FASEB J 2008; 22:2084-2089
[6] de M A, Punshon G, Ramesh B, et al. In situ endothelialization potential of a biofunctionalised nanocomposite biomaterial-based small diameter bypass graft. Biomed Mater Eng 2009; 19:317-331
[7] Kidane A G, Burriesci G, Edirisinghe M, Ghanbari H, Bonhoeffer P, Seifalian A M. A novel nanocomposite polymer for development of synthetic heart valve leaflets. Acta Biomater 2009; 5:2409-17.
[8] Grillo H C. Development of tracheal surgery: treatment of tracheal diseases. Ann Thorac Surg. 2003; 75:1039-47
[9] Haas R, Murea S. The role of granulocyte colony-stimulating factor in mobilization and transplantation of peripheral blood progenitor and stem cells. Cytokines Mol Ther. 1995; 1: 249-70.
[10] Jia Y, Warin R, Yu X, Epstein R, Noguchi C T. Erythropoietin signalling promotes transplanted progenitor cell survival. FASEB J. 2009; 23(9):3089-99.
[11] Brines M, Cerami A. Erythropoietin-mediated tissue protection: reducing collateral damage from the primary injury response. J Intern Med. 2008; 264(5):405-32.
[12] Dal Pozzo S, Urbani S, Mazzanti B, et al. High recovery of mesenchymal progenitor cells with non-density gradient separation of human bone marrow. Cytotherapy. 2010; 12(5):579-86.
[13] Ronzière M C, Perrier E, Mallein-Gerin F, Freyria A M. Chondrogenic potential of bone marrow- and adipose tissue-derived adult human mesenchymal stem cells. Biomed Mater Eng. 2010 1; 20(3):145-58.
[14] Bouffi C, Thomas O, Bony C, et al. The role of pharmacologically active microcarriers releasing TGF-beta3 in cartilage formation in vivo by mesenchymal stem cells. Biomaterials. 2010; 31(25):6485-93.
[15] Bader A, Macchiarini P. Moving towards in situ tracheal regeneration: the bionic tissue engineered transplantation approach. J Cell Mol Med. 2010; 14(7):1877-89.
[16] Macchiarini P. Primary tracheal tumours. Lancet Oncol 2006; 7: 83-91.

The invention is further described by the following numbered paragraphs:

1. A method of producing a synthetic scaffold for replacing an airway or portion thereof, the method comprising:
placing one or more structural ribs on an airway mold, wherein each structural rib comprises a first material,
coating the airway mold and structural ribs with a second material, and
solidifying the second material to form a conduit that comprises the structural ribs.
2. The method of paragraph 1, wherein the first material is a set POSS-PCU nanocomposite material.
3. The method of paragraph 2, wherein the second material is a POSS-PCU fluid and the solidifying comprises coagulating the POSS-PCU fluid.
4. The method of paragraph 1, wherein the airway mold comprises a convex anterior and a straight posterior.
5. The method of paragraph 1, wherein each structural rib is U-shaped.
6. The method of paragraph 1, wherein the airway mold is a glass, stainless steel, or PTFE mold.
7. The method of paragraph 1, wherein each structural rib is about 0.5 cm thick.
8. The method of paragraph 1, wherein the structural ribs are separated by about 0.5 cms along the length of the airway mold.
9. The method of paragraph 1, wherein the airway mold is a tracheal mold having a diameter of approximately 2-3 cm.
10. The method of paragraph 9, wherein each structural rib has an internal width of about 2-3 cm.
11. The method of paragraph 1, wherein the airway mold is a bronchial mold having a diameter of approximately 1-1.5 cm.
12. The method of paragraph 11, wherein each structural rib has an internal width of about 1-1.5 cm.
13. The method of paragraph 1, wherein the airway mold is branched and includes one tracheal segment and two bronchial segments.
14. The method of paragraph 13, wherein the airway mold includes a detachable bronchial segment.
15. The method of paragraph 1, wherein the conduit is porous.
16. The method of paragraph 15, wherein the second material is a POSS-PCU polymer fluid that comprises salt crystals, and wherein the POSS-PCU polymer is coagulated in an aqueous solution, and wherein the salt crystals are dissolved after coagulation to form pores.
17. The method of paragraph 15, wherein the average pore diameter is 20-100 microns.
18. The method of paragraph 17, wherein the average pore diameter is about 40 microns.
19. The method of paragraph 16, wherein the salt is sodium bicarbonate.
20. A method of seeding a synthetic airway scaffold, the method comprising incubating a synthetic airway scaffold in a rotating bioreactor in the presence of a cellular solution.
21. The method of paragraph 20, wherein the synthetic airway scaffold was produced according to any one of methods 1-19.
22. The method of paragraph 20, wherein the cells are mesenchymal cells.
23. The method of paragraph 20, wherein the cells are obtained from human bone marrow.
24. The method of paragraph 20, wherein the incubating lasts for 1-3 days.
25. The method of paragraph 20, wherein the incubating lasts for 2 days.
26. The method of paragraph 20, wherein the incubating is at a temperature of between about 25 C and 37 C.
27. The method of paragraph 26, wherein the temperature is about 30 C.

28. The method of paragraph 26, wherein the temperature is about 35 C.

29. The method of any one of paragraphs 1-28, further comprising adding epithelial cells.

30. A method of preparing a seeded synthetic scaffold for transplantation, the method comprising adding one or more growth factors to the seeded scaffold.

31. The method of paragraph 30, wherein the synthetic scaffold was produced according to any one of paragraphs 1-29.

32. The method of paragraph 30, wherein the scaffold was seeded according to any one of paragraphs 20-31.

33. The method of any one of paragraphs 1-32, wherein a first growth factor is added to a structural rib of the synthetic scaffold.

34. The method of paragraph 33, wherein the first growth factor promotes cartilage formation.

35. The method of paragraph 34, wherein the first growth factor is TGF-β.

36. The method of paragraph 33, wherein the first growth factor is injected into the structural rib.

37. The method of any prior paragraph, wherein a second growth factor is added to the wall of the synthetic scaffold.

38. The method of paragraph 37, wherein the second growth factor promotes cell mobilization and proliferation.

39. The method of paragraph 38, wherein the second growth factor is GCSF.

40. The method of any prior paragraph, further comprising adding EPO to the seeded synthetic scaffold, wherein EPO is added in an amount sufficient to prevent apoptosis.

Having thus described in detail preferred embodiments of the present invention, it is to be understood that the invention defined by the above paragraphs is not to be limited to particular details set forth in the above description as many apparent variations thereof are possible without departing from the spirit or scope of the present invention.

What is claimed is:

1. A method of producing a synthetic scaffold of claim for replacing an airway or portion thereof, the method comprising:

placing one or more structural ribs on an airway mold, wherein each structural rib comprises a first material, coating the airway mold and one or more structural ribs with a polyhedral oligomeric silsesquioxane covalently bonded to poly(carbonate-urea)urethane (POSS-PCU) fluid, and coagulating the POSS-PCU fluid to form a conduit that comprises the one or more structural ribs.

2. The method of claim 1, wherein the first material is a set POSS-PCU nanocomposite material.

3. The method of claim 1, wherein the airway mold comprises a convex anterior and a straight posterior.

4. The method of claim 1, wherein each structural rib is U-shaped.

5. The method of claim 1, wherein the airway mold is a glass, stainless steel, or PTFE mold.

6. The method of claim 1, wherein each structural rib is about 0.5 cm thick.

7. The method of claim 1, wherein the structural ribs are separated by about 0.5 cms along the length of the airway mold.

8. The method of claim 7, wherein the airway mold is a tracheal mold having a diameter of approximately 2-3 cm.

9. The method of claim 8, wherein each structural rib has an internal width of about 2-3 cm.

10. The method of claim 1, wherein the airway mold is a bronchial mold having a diameter of approximately 1-1.5 cm.

11. The method of claim 10, wherein each structural rib has an internal width of about 1-1.5 cm.

12. The method of claim 1, wherein the airway mold is branched and includes one tracheal segment and two bronchial segments.

13. The method of claim 12, wherein the airway mold includes a detachable bronchial segment.

14. The method of claim 1, wherein the conduit is porous.

15. The method of claim 1, wherein the POSS-PCU polymer fluid comprises salt crystals, and wherein the POSS-PCU polymer is coagulated in an aqueous solution, and wherein the salt crystals are dissolved after coagulation to form pores.

16. The method of claim 14, wherein the average pore diameter is 20-100 microns.

17. The method of claim 15, wherein the average pore diameter is about 40 microns.

18. The method of claim 14, wherein the salt is sodium bicarbonate.

* * * * *